US00PP15395P2

(12) United States Plant Patent
DeBelder

(10) Patent No.: US PP15,395 P2
(45) Date of Patent: Dec. 7, 2004

(54) ***HYDRANGEA* PLANT NAMED 'LITTLE LAMB'**

(50) Latin Name: *Hydrangea paniculata*
Varietal Denomination: Little Lamb

(75) Inventor: Jelena DeBelder, Essen (BE)

(73) Assignee: Spring Meadow Nursery Inc., Grand Haven, MI (US)

( * ) Notice: Subject to any disclaimer, the term of this patent is extended or adjusted under 35 U.S.C. 154(b) by 100 days.

(21) Appl. No.: 10/303,469

(22) Filed: Nov. 25, 2002

(51) Int. Cl.[7] ..... A01H 5/00
(52) U.S. Cl. ..... Plt./250
(58) Field of Search ..... Plt./250

*Primary Examiner*—Howard J. Locker
(74) *Attorney, Agent, or Firm*—C. A. Whealy

(57) ABSTRACT

A distinct cultivar of *Hydrangea* plant named 'Little Lamb', characterized by its upright and outwardly arching plant habit; inflorescences held upright and outward on strong stems; compact, dense and conical-shaped inflorescences; and numerous flowers per inflorescence.

1 Drawing Sheet

Botanical classification/cultivar designation: *Hydrangea paniculata* cultivar Little Lamb.

BACKGROUND OF THE INVENTION

The present Invention relates to a new and distinct cultivar of *Hydrangea* plant, botanically known as *Hydrangea paniculata*, and hereinafter referred to by the cultivar name Little Lamb.

The new *Hydrangea* originated from a cross-pollination during the summer of 1989 of a proprietary selection of *Hydrangea paniculata* identified as code number 16, not patented, as the female, or seed, parent with an unknown selection of *Hydrangea paniculata*, not patented, as the male, or pollen, parent. The cultivar Little Lamb was discovered and selected by the Inventor as a single plant within the progeny of the stated cross-pollination in a controlled environment in Essen, Belgium.

Asexual reproduction of the new cultivar by softwood cuttings taken in Essen, Belgium since 1995, has shown that the unique features of this new *Hydrangea* are stable and reproduced true to type in successive generations.

SUMMARY OF THE INVENTION

Plants of the cultivar Little Lamb have not been observed under all possible environmental conditions. The phenotype may vary somewhat with variations in environment such as temperature and light intensity without, however, any variance in genotype.

The following traits have been repeatedly observed and are determined to be the unique characteristics of 'Little Lamb'. These characteristics in combination distinguish 'Little Lamb' as a new and distinct cultivar:

1. Upright and outwardly arching plant habit.
2. Inflorescences held upright and outward on strong stems.
3. Compact, dense and conical-shaped inflorescences.
4. Numerous flowers per inflorescence.

Plants of the new *Hydrangea* differ from plants of female parent selection in the following characteristics:

1. Inflorescences of plants of the new *Hydrangea* are smaller and more dense than inflorescences of plants of the female parent selection.
2. Plants of the new *Hydrangea* have smaller flowers than plants of the female parent selection.

Plants of the new *Hydrangea* can be compared to plants of the *Hydrangea paniculata* cultivar P.G., not patented. In side-by-side comparisons conducted in Grand Haven, Mich., plants of the new *Hydrangea* differed from plants of the cultivar P.G. in the following characteristics:

1. Plants of the new *Hydrangea* were smaller than plants of the cultivar P.G..
2. Plants of the new *Hydrangea* had larger inflorescences than plants of the cultivar P.G..
3. Plants of the new *Hydrangea* had smaller flowers than plants of the cultivar P.G..

Plants of the new *Hydrangea* can also be compared to plants of the *Hydrangea paniculata* cultivar Tardiva, not patented. In side-by-side comparisons conducted in Grand Haven, Mich., plants of the new *Hydrangea* differed from plants of the cultivar Tardiva in the following characteristics:

1. Plants of the new *Hydrangea* were smaller than plants of the cultivar Tardiva.
2. Plants of the new *Hydrangea* had larger and more dense inflorescences than plants of the cultivar Tardiva.
3. Plants of the new *Hydrangea* had smaller flowers than plants of the cultivar Tardiva.
4. Plants of the new *Hydrangea* flowered earlier than plants of the cultivar Tardiva.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea*.

The photograph at the top of the sheet is a side perspective view of a typical plant of 'Little Lamb'.

The photograph at the bottom of the sheet comprises a close-up view of a typical inflorescence of 'Little Lamb'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. Plants were about 3.5 years old when the photographs and description were taken. Photographs and description were taken during the summer when the plants were in full flower.

Botanical classification: *Hydrangea paniculata* cultivar Little Lamb.

Parentage:

*Male, or pollen, parent.*—Proprietary selection of *Hydrangea paniculata* identified as code number 16, not patented.

*Female, or seed, parent.*—Unknown *Hydrangea paniculata* selection, not patented.

Propagation:

*Type cutting.*—By softwood cuttings.

*Time to initiate roots.*—About 12 days at 25° C.

*Time to produce a rooted cutting or liner.*—About 90 days at 25°C.

*Root description.*—Thick, fibrous.

*Rooting habit.*—Freely branching, dense.

Plant description:

*Form/growth habit.*—Upright and outwardly arching plant habit; bushy perennial shrub. Rounded and moderately vigorous.

*Usage.*—Appropriate for one to three-gallon containers.

*Plant height, soil level to top of plant plane.*—About 50 cm.

*Plant diameter or area of spread.*—About 50 cm.

*Branching habit.*—When pruned, freely branching with potentially about 96 lateral branches per plant.

*Lateral branches.*—Length: About 29 cm. Diameter: About 4 to 5 mm. Internode length: About 6 cm. Texture: Glabrous. Color: 177A.

*Foliage description.*—Arrangement: Typically opposite, occasionally whorled. Length: About 9 to 9.5 cm. Width: About 4 to 5 cm. Shape: Lanceolate to ovate. Apex: Acuminate. Base: Obtuse. Margin: Serrulate. Texture, upper and lower surfaces: Pubescent; rugose. Venation pattern: Pinnate. Color: Young and fully expanded foliage, upper surface: 137B. Young and fully expanded foliage, lower surface: 138A. Venation, upper surface: 138A. Venation, lower surface: 138B. Petiole: Length: About 1 to 1.5 cm. Diameter: About 1.5 mm. Color: 138B.

Flower description:

*Flower type and habit.*—Single fertile and sterile flowers arranged on terminal panicles; panicles compact, dense and conical in shape. Sterile flowers with large showy sepals and without petals and reproductive organs. Fertile flowers small with petals, sepals and reproductive organs. Sterile flowers persistent; fertile flowers not persistent. Flowers not fragrant.

*Natural flowering season.*—Continuously flowering during the summer in Grand Haven, Mich.

*Flower longevity.*—Sterile flowers last about 90 days on the plant; fertile flowers last about one week on the plant.

*Quantity of flowers.*—Freely flowering; about 1292 sterile flowers and about 627 fertile flowers per panicle.

*Flower diameter.*—Fertile flowers: About 3 mm. Sterile flowers: About 1.5 cm.

*Flower depth (height).*—Fertile flowers: About 3 mm. Sterile flowers: About 6 mm.

*Flower buds (fertile and sterile flowers).*—Length: About 1 mm. Diameter: About 1.5 mm. Shape: Obovate to rounded. Color: 142B to 157B.

*Petals (petals present only on fertile flowers; sterile flowers do not have petals).*—Arrangement: About five. Length: About 2 mm. Width: About 1 mm. Shape: Lanceolate. Apex: Acute. Base: Attenuate. Margin: Entire. Texture, upper and lower surfaces: Smooth, glabrous. Color: When opening and fully opened, upper surface: 155A; color becoming closer to 157A with development. When opening and fully opened, lower surface: 155A.

*Sepals.*—Quantity per flower: Fertile flowers: About five, fused into a calyx. Sterile flowers: About four. Length: Fertile flowers: About 0.5 mm. Sterile flowers: About 7 mm. Width: Fertile flowers: Less than 0.5 mm. Sterile flowers: About 5 mm. Shape: Fertile flowers: Connate. Sterile flowers: Elliptic. Apex: Fertile flowers: Acute. Sterile flowers: Obtuse. Base: Fertile flowers: Fused. Sterile flowers: Attenuate. Margin, fertile and sterile flowers: Entire. Texture, fertile and sterile flowers, upper and lower surfaces: Smooth, glabrous. Color: Fertile flowers: When opening and fully opened, upper and lower surfaces, 157B. Sterile flowers: When opening and fully opened, upper surface: 155A; color becoming closer to 157A with development. When opening and fully opened, lower surface: 155A.

*Pedicels.*—Angle: Fertile flowers: About 90 to 150° from vertical. Sterile flowers: About 150° from vertical. Strength, fertile and sterile flowers: Strong. Length: Fertile flowers: About 1 mm. Sterile flowers: About 1 cm. Color, fertile and sterile flowers: 155A to 157B.

*Reproductive organs (reproductive organs present only on fertile flowers; sterile flowers do not have reproductive organs).*—Stamens: Quantity per flower: About ten. Anther shape: Round. Anther length: Less than 1 mm. Anther color: 155A. Pollen amount: Scarce. Pollen color: 157A. Pistils: Pistil quantity per flower: Three, fused. Pistil length: About 0.5 mm. Stigma shape: Three-lobed. Stigma color: 157B. Style length: About 0.5 mm. Style color: 157B. Ovary color: 142C. Seed: Length: Less than 0.5 mm. Diameter: Less than 0.5 mm. Color: Brown.

Disease/pest resistance: Under commercial production conditions, plants of the new *Hydrangea* have not been observed to be resistant to pathogens or pests common to *Hydrangea*.

Weather tolerance: Plants of the new *Hydrangea* have been shown to be tolerant to temperatures ranging from −30 to 33° C. Flowers of plants have exhibited excellent tolerance to wind and rain.

It is claimed:

1. A new and distinct cultivar of *Hydrangea* plant named 'Little Lamb', as illustrated and described.

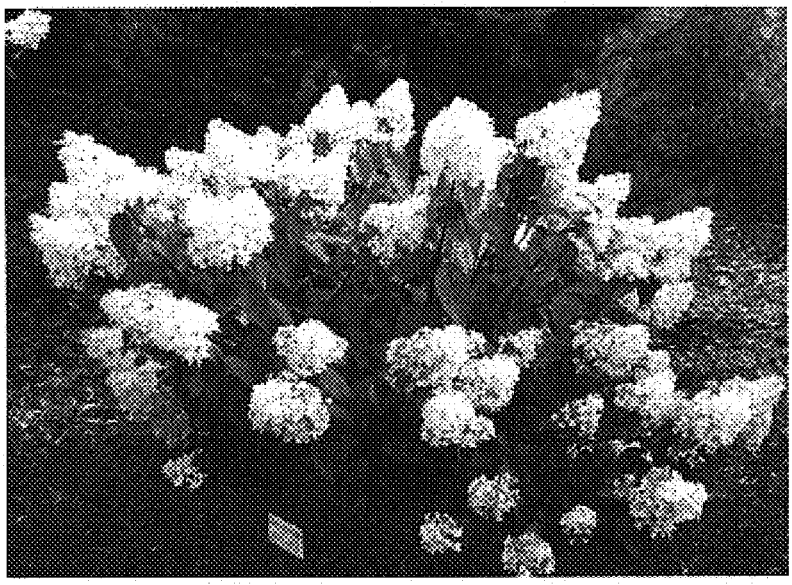
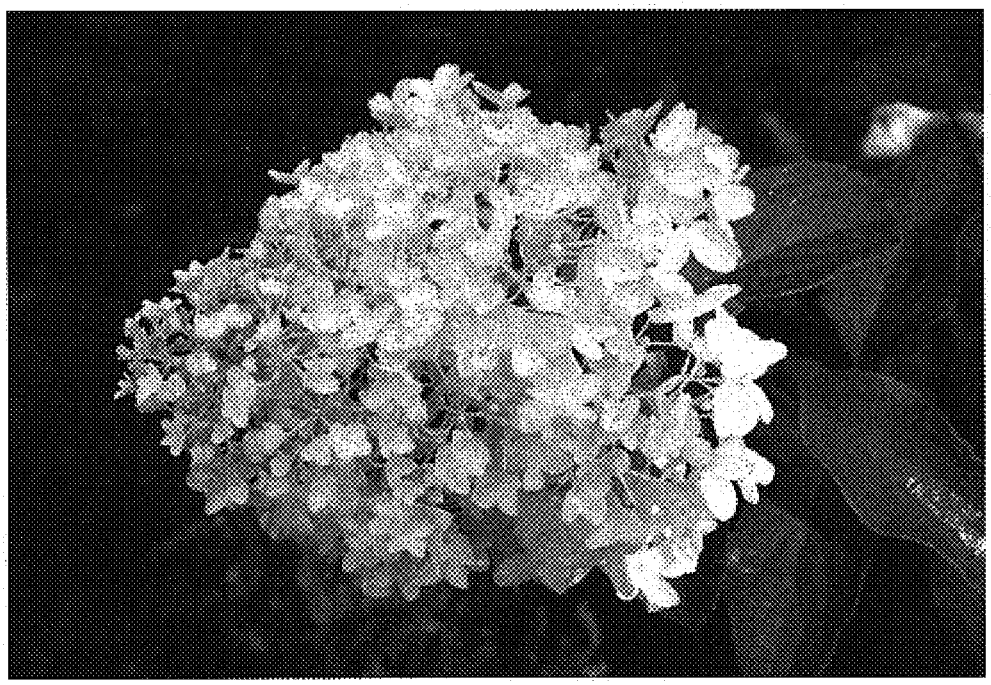

* * * * *